US009510521B2

(12) United States Patent
Venburg et al.

(10) Patent No.: US 9,510,521 B2
(45) Date of Patent: *Dec. 6, 2016

(54) USE OF ABSCISIC ACID TO ALTER SENSORY CHARACTERISTICS OF RED GRAPES AND WINE

(75) Inventors: Gregory D. Venburg, Deerfield, IL (US); Andrew Rath, Box Hill (AU); Peter D. Petracek, Grayslake, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 1359 days.

This patent is subject to a terminal disclaimer.

(21) Appl. No.: 12/011,922

(22) Filed: Jan. 30, 2008

(65) Prior Publication Data

US 2008/0293574 A1 Nov. 27, 2008

Related U.S. Application Data

(60) Provisional application No. 60/898,470, filed on Jan. 31, 2007, provisional application No. 60/936,395, filed on Jun. 20, 2007, provisional application No. 60/958,321, filed on Jul. 3, 2007.

(51) Int. Cl.
*A01N 37/42* (2006.01)
*A01G 17/02* (2006.01)
*A01G 7/06* (2006.01)
*A01N 25/02* (2006.01)
*A01N 25/00* (2006.01)

(52) U.S. Cl.
CPC ............... *A01G 17/02* (2013.01); *A01G 7/06* (2013.01); *A01N 25/00* (2013.01); *A01N 25/02* (2013.01); *A01N 37/42* (2013.01)

(58) Field of Classification Search
CPC .......... A01G 17/02; A01G 7/06; A01N 37/42; A01N 25/00; A01N 25/02
USPC ....................................................... 424/320
See application file for complete search history.

(56) References Cited

U.S. PATENT DOCUMENTS

2005/0198896 A1 9/2005 Quaghebeur

FOREIGN PATENT DOCUMENTS

JP 03157305 A * 7/1991

OTHER PUBLICATIONS

JP 03157305, Shirai, M. et al., Agent for increasing weight of grapes containing abscisic acid, 1991, Derwent Abstract, pp. 1-3.*
Jeong, S.T. et al., Effects of Plant Hormones and Shading on the Accumulation of Anthocyanins and the Expression of Anthocyanin Biosynthetic Genes in Grape Berry Skins, 2004, Plant Science, vol. 167, pp. 247-252.*
Wheeler, S., The Role of Abscisic Acid in Grape Berry Development, Oct. 2006, Thesis for Doctor of Philosophy, The Unversity of Adelaide, School of Agriculture and Wine Discipline of Horticulture. Retrieved from the Internet: <URLhttp://digital.library.adelaide.edu.au/dspace/bitstream/2440/57767/1/02whole.pdf>, pp. 1 and 103-131.*
Kim et al., Effects of Ehtephon and ABA Application on Sugar and Organic Acid Content in Grapes (Vitis spp.), 1998, J. Kor. Soc. Hort. Sci., vol. 39, Issue 5, pp. 542-546.*
Hellman, E., Exogenously Applied Abscisic Acid Did Not Consistently Delay Budburst of Deacclimating Grapevines, 2006, Journal of the American Pomological Society, vol. 60, Issue 4, pp. 178-186.*
Peppi, M.C., Abscisic Acid Application Timing and Concentration Affect Firmness, Pigmentation, and Color of Flame Seedless Grapes, 2006, HortScience, vol. 41, Issue 6, pp. 1440-1445.*
Roussouw et al., "The Phenolic Composition of South African Pinotage, Shiraz and Cabernet Sauvignon Wines", South African Journal of Enology and Viticulture, 2004, 25(2) pp. 94-104.
EP Search Report issued Dec. 15, 2011.
Susan Faith Wheeler, "The role of abscisic acid in grape berry development", Oct. 2006, pp. 1-176, XP007919419.
Canton et al., "Varietal differences among the polyphenol profiles of seven table grap cultivars studied by LC-DAD-MS-MS", J. Agric. Food Chem. 2002, 50, pp. 5691-5696, XP007919425.
Byun et al., (English Translation) "Effects of GA3, thidiazuron and ABA on fruit set and quality of 'Kyoho' grapes" J. Kor. Soc. Hort. Sci., 1995, vol. 36, pp. 231-239.
Kim et al., (English Translation) "Effects of Ethephon and ABA Application on Sugar and Organic Acid Content in Grapes", Jour. Kor. Soc. Hort. Sci., 1998, 39(5), pp. 542-546.
Williams, "Scientific apparatus and laboratory methods", Science, New Series, vol. 101, No. 2625, Apr. 20, 1945, pp. 416-417.
Darrieutort et al., "Evaluation of a trunk injection technique to control grapevine wood diseases", Plsytopathol, Mediterr., 2007, 46, pp. 50-57.
Reynolds et al., "NM and paclobutrazol control grapevine suckers: vine performance and fruit tissue residues", HortScience, 26(1), 1991, pp. 1286-1287.
Aloni et al., "The never ripe mutant provides evidence that tumor-induced ethylene controls the morphogenesis of agrobacterium tumefaciens-induced crown galls on tomato stems", Plant Phystol., 1998, 117, pp. 841-849.
Sterrett, "Paclobutrazol: a promising growth inhibitor for injection into woody plants", J. Amer. Soc. Hort. Sci., 110(1), 1985, pp. 4-8.
Bailey et al., "BMPs for PGRs to maximize efficacy of plant growth regulators, follow these application guidelines", Ornamental Outlook, Aug. 2004, pp. 25, 26, 28, 30.
Tardieu et al., "Stomata control by both [ABA] in the xylem sap and leaf water status: a test of a model for droughted or ABA-fed field-grown maize", Plant, Cell and Environment, 1993, 16, pp. 413-420.
Wang, et al., "Translocation of paclobutrazol, a gibberellin biosynthesis inhibitor, in apple seedlings", Plant Phys., 1986, 82:11-14.

(Continued)

*Primary Examiner* — John Pak
*Assistant Examiner* — Andriae M Holt
(74) *Attorney, Agent, or Firm* — Wood, Phillips, Katz, Clark & Mortimer

(57) ABSTRACT

This invention describes the use of S-abscisic acid (S-ABA) to modify sensory characteristics such as aroma, bouquet, flavor, mouthfeel, astringency, balance, complexity or finish of red grapes and red wine.

1 Claim, No Drawings

(56) References Cited

OTHER PUBLICATIONS

Edgerton et al., "Some effects of paclobutrazol on growth and fruiting of apple, peach and cherry", Acta Horticulture 179, 1986, Growth Regulators, pp. 467-472.
Greene et al., "Mode of action of benzyladenine when used as a chemical thinner on apples", J. Amer. Soc. Hort. Sci., 117(5), 1992, pp. 775-779.
Bukovac et al., "Characterizing pesticide and surfactant penetration with isolated plant cuticles", Pestic. Sci. 37, 1997, pp. 179-194.
Sharma et al., "Bahaviour of forchlorfenuron residues in grape, soil and water". Chemosphere, 2003, 50, pp. 589-594.
Weaver et al., "Effect of ethephon on coloration and maturation of wine grapes", Amer. J. Enol, Viticult., vol. 25, No. 1, 1974, pp. 39-41.
Zucconi et al., "Approaches to phytohormone studies on regulation of plant processes a reassessment", Department of Horticulture, Michigan State University, Journal Article No. 10006, pp. 1-14.
Gu et al., "Efficacy, rate and timing of applications of abscisic acid to enhace fruit anthocyanin contents in 'Cabernet Sauvignon' grapes", Journal of Horticultural Science & Biotechnology, 86(5), 2011, pp. 505-510.
Lawless, et al., Evaluation of Wine Quality Using a Small Panel Hedonic Scale Method, Journal of Sensory Studies, 12(4):317-332, 1997.

\* cited by examiner

USE OF ABSCISIC ACID TO ALTER SENSORY CHARACTERISTICS OF RED GRAPES AND WINE

FIELD OF THE INVENTION

The present invention is directed to the use of S-abscisic acid and its salts to modify the development of the sensory characteristics of red grapes and red wine, such as aroma, bouquet, flavor, mouthfeel, astringency, balance, complexity or finish.

BACKGROUND OF THE INVENTION

Abscisic acid (S-Abscisic acid, S-ABA, ABA) is a natural occurring plant hormone found in all higher plants (Cutler and Krochko. 1999. Trends in Plant Science. 4: 472-478. Finkelstein and Rock. 2002. The Arabidopsis Book. ASPB, Monona, Md., 1-52). S-ABA is involved in many major processes during plant growth and development including dormancy, germination, bud break, flowering, fruit set, general growth and development, stress tolerance, ripening, maturation, organ abscission, and senescence. S-ABA also plays an important role in plant tolerance to environmental stresses, such as drought, cold, and excessive salinity.

One key role of S-ABA in regulating physiological responses of plants is to act as a signal of reduced water availability to reduce water loss, inhibit growth and induce adaptive responses. All these functions are related to stomatal closure of plant leaves (Raschke and Hedrich, 1985, Planta, 163: 105-118). When stomata close, plants conserve water to survive in environmental stresses. However, stomatal closure also can result in the reduction of photosynthesis, and respiration and thus growth. Stomatal closure is a rapid response of plants to S-ABA. The mechanism of action of S-ABA-induced stomatal closure has been studied, and the effect has been shown to be due primarily to S-ABA's effect on guard cell ion channels. Specifically, S-ABA blocks $H^+$ extrusion and $K^+$ influx from guard cells and promotes $K^+$, $Cl^-$, and malate extrusion and $Ca^{2+}$ influx. The net effect of S-ABA is to reduce the total osmotica in the guard cells, which in turn decreases the water content in the cell. This causes the guard cells to lose their turgor and thus close the stomata (Assmann 2004 In: *Plant Hormones Biosynthesis, Signal Transduction, Action*! ed. Davies, p 391-412). The closing of stomata results in reduced transpiration of the plant leaf. In grapes, application of S-ABA has been reported to increase stomatal resistance in grapevines, thereby reducing the gas exchange and stomatal transpiration of the leaves (Düring and Broquedis, 1980, Sci. Hort., 13: 253-260).

The exogenous application of S-ABA to red grapes prior to harvest has been shown to increase the accumulation of anthocyanins and increase the red color of the grape berry skins (e.g. Han, D. H, S. M. Lee, and S. B. Kim. 1996, J. Kor. Soc. Hort. Sci. 37: 416-420; Lee, K. S., J. C. Less, Y. S. Hwang, and I. B. Hur, 1997, J. Kor. Soc. Hort. Sci. 38: 717-721; Kondo, S., Masuda, E. and Inoue, K., 1998, Acta Hort., 464: 35-40; Pepe, M. C., Fidelibus, M. W., Dokoozlian, N. 2006, HortScience, 41:1440-1445).

The sensory characteristics of wine such as aroma and flavor are complex and there is interest in altering wine grape berry and/or wine characteristics to produce more diverse or better wine, or wines with different balances of sensory characteristics. A patent application has been filed (Quaghebeur, K., 2005, US 2005/0198896 A1) claiming that ABA application enhances wine quality as a consequence of simulating drought in the grapevine leading to reduction in grape berry size in conjunction with increased sugar content. However, no mention is made of ABA application affecting sensory characteristics such as aroma, bouquet, flavor, mouthfeel, astringency, balance, complexity or finish. The literature reports that the effect of S-ABA application on grapes is to increase berry and cluster weight (Han, D. H, S. M. Lee, and S. B. Kim. 1996. J. Kor. Soc. Hort. Sci. 37: 416-420). While the effect of S-ABA to increase red color of red grapes has been studied and reported, there are no previous reports on the effect of and the use of S-ABA on red grapes to affect the various sensory characteristics of red grapes and/or the resulting wine.

SUMMARY OF THE INVENTION

The present invention is directed to the preharvest treatment of red wine grapes with S-ABA or its salts after fruit set. This treatment alters the development of red grape berry and wine flavor characteristics, allowing the berry and wine sensory characteristics, such as aroma, bouquet, flavor, mouthfeel, astringency, balance, complexity or finish to be manipulated to help achieve the wine style desired by the viticulturist and winemaker.

DETAILED DESCRIPTION OF THE INVENTION

The present invention comprises the application of S-ABA or its salts to red grape grapevines to modify development of grape berry and wine sensory characteristics. S-ABA or a salt of S-ABA is applied to the grapevines as a foliar spray to the grape berries and leaves, by application to the roots of the grapevine through irrigation or fertigation methods, or by injection into the grapevine.

Abscisic acid (S-ABA; ABA; S-(+)-abscisic acid; +-ABA, (+)-(S)-cis,trans-abscisic acid, (+)-(S)-cis,trans-ABA; S-ABA; (S)-5-(1-hydroxy-2,6,6,-trimethyl-4-oxo-2-cyclohexen-1-yl)-3-methyl-(2Z,4E)-pentadienoic acid; CAS registry no. [21293-29-8]) is available from Lomon Bio-Technology Co., Ltd. (Shichuan, China).

Suitable salts of S-ABA include, but are not limited to sodium, potassium, calcium, ammonium, magnesium and amine salts.

S-ABA or its salts is applied to the grapevines after berry set to achieve the desired effect on the sensory characteristics of the grape berries and wine. The presently preferred timing of the S-ABA application is during the period of pre-veraison (approximately 3 weeks before veraison, where veraison is defined as berry softening) through the post-veraison period (when sugar levels in berries measure approximately 18-20° brix (10-11 Baume)).

Water is used as the carrier solvent for the applications. In the present invention, surfactants can be added to the chemical solution to improve the performance of the S-ABA or its salts, particularly for the foliar application. The water solution may contain between 0.01% to 0.5% v/v of a surfactant, such as Tween 20 (available from Sigma-Aldrich, St. Louis, Mo.).

The presently preferred surfactant for S-ABA or S-ABA salt performance is Brij 98 (polyoxyethylene (20) oleyl ether) available from Uniqema (Castle, Del.). Other surfactants are also useful in the present invention, including but not limited to, other surfactants in the Brij family (polyoxyethylene fatty alcohol ether) available from Uniqema (Castle, Del.), surfactants in the Tween family (Polyoxyethylene sorbitan ester) available from Uniqema (Castle, Del.), the Silwet family (Organosilicone) available from Momentive Performance Materials (Wilton, Conn.), the Triton family (Octylphenol ethoxylate) available from The Dow Chemical Company (Midland, Mich.), the Tomadol family (ethoxylated linear alcohol) available from Tomah3 Products, Inc. (Milton, Wis.), the Myrj family (Polyoxyethylene (POE) fatty acid ester) available from Uniqema (Castle, Del.), the Span family (Sorbitan ester) available from Uniqema (Castle, Del.), and the Trylox family (Ethoxylated Sorbitol and Ethoxylated Sorbitol Ester) available from Cognis Corporation (Cincinnati, Ohio) as well as commercial surfactants such as Latron B-1956 (77.0% modified phthalic/glycerol alkyl resin and 23.0% Butyl alcohol) available from Dow AgroSciences LLC (Indianapolis, Ind.), Capsil (Blend of Polyether-polymethylsiloxanecopolymer and nonionic surfactant) available from Aquatrols (Paulsboro, N.J.), Agral 90 (Nonyl phenol ethoxylate) available from Norac Concept. Inc. (Orleans, Ontario, Canada), Kinetic (99.00% proprietary blend of polyalkyleneoxide modified polydimethylsiloxane and nonionic surfactants) available from Setre Chemical Company (Memphis, Tenn.), and Regulaid (90.6% 2-butoxyethanol, poloxalene, monopropylene glycol) available from KALO, Inc. (Overland Park, Kans.).

Other additives are also useful in the present invention including, but not limited to, urea, nitrate salts such as ammonium nitrate, salts such as calcium chloride, humectants such as poly(ethylene glycol), and vegetable oils such as soybean oil, corn oil, cotton oil, and palm oil.

The effective concentration range of the active ingredient S-ABA varies depending on the water volume applied as well as other factors such as the plant variety, height, age, desired duration of effect and application method. The S-ABA concentration range is from about 1-about 10,000 ppm S-ABA. The preferred S-ABA concentration range for foliar applications is about 50-about 500 ppm. The preferred application volume for foliar applications is about 25-about 300 gallons/A. Foliar spray applications are directed at the grape bunches to achieve complete coverage of the grapes bunches and to maximize the effect of the S-ABA application. Soil applications are directed towards the rooting zone. Application methods include, but are not limited to application through irrigation/fertigation dripper line- or application of S-ABA formulations or solutions to the soil at the base of the vine, followed by application of water to the soil to transport the S-ABA to the roots of the vine.

EXAMPLES

The following examples illustrate that application of S-ABA to red grapes alters wine sensory characteristics.

Example 1

S-ABA (200 ppm) was applied by foliar spray using a standard vineyard airblast sprayer at 2000 L/ha to commercially grown Shiraz grapes approximately 3 weeks prior to initiation of veraison. The spray mix contained the surfactant/wetter Agral at 10 ml/100 L. Results reported are means of 4 replicates (grapes) and 3 replicates (wines) per treatment. Winemaking followed a standard small lot fermentation protocol with each replicate wine being made from 50 kg of harvested grapes.

Table 1 shows that S-ABA does not affect at-harvest grape sugar, pH, or total acidity or wine pH. However, at-harvest grape anthocyanin and wine color density and total phenolics are increased by S-ABA.

TABLE 1

Effect of abscisic acid (S-ABA) on Shiraz grape quality at harvest and wine quality.

|  | Untreated | S-ABA treated |
|---|---|---|
| Grapes at harvest | | |
| Sugar (Be) | 13.6 | 13.8 |
| pH | 4.1 | 4.1 |
| Total acidity | 4.3 | 4.2 |
| Anthocyanins (mg/g) | 0.92 | 1.02 |
| Wine | | |
| pH | 3.75 | 3.76 |
| Wine color density (a.u.) | 5.52 | 7.23 |
| Wine hue | 0.58 | 0.56 |
| Total phenolics | 23.84 | 29.94 |

Table 2 shows the sensory profile as determined by 10 experienced sensory assessors. Shiraz wine made from S-ABA-treated fruit were described as have a more intense berry aroma and a more fruity, more acidic taste. Using a nine-point hedonic scale rating (dislike=1 to like=9) the sensors judged wine from the S-ABA treatment higher than the untreated (6.2 vs. 5.0, respectively) and thus a technically better wine.

TABLE 2

Effect of abscisic acid (S-ABA) on Shiraz wine sensory profile.

| Character | Untreated | S-ABA treated |
|---|---|---|
| Aroma | Berry, vegetal | More intense berry |
| Taste | Dark fruit, soft tannins | More fruity, more acidic |
| Color | Red, purple hues | Increased intensity |
| Hedonic scale (1-dislike, 9 like) | 5.0 | 6.2 |

Example 2

S-ABA (200 ppm) was applied by foliar spray to Cabernet Sauvignon grapes when sugar levels were approximately 11 Be using a standard vineyard airblast sprayer at approximately 2000 L/ha. The spray mix contained the surfactant/wetter Agral at 10 ml/100 L. Wine was prepared from the treated and untreated grapes. Table 3 shows that S-ABA did not affect sugar, pH, total acidity, and anthocyanins of grapes at harvest and did not affect the alcohol, pH, wine color density, wine hue, and total phenolics of the wine.

TABLE 3

Effect of abscisic acid (S-ABA) on Cabernet Sauvignon grape quality at harvest and wine quality.

|  | Untreated | S-ABA treated |
|---|---|---|
| Grapes at harvest | | |
| Sugar (Be) | 12.9 | 13.1 |
| pH | 3.94 | 3.97 |
| Total acidity | 4.9 | 4.9 |
| Anthocyanins (mg/g) | 0.91 | 0.93 |
| Wine | | |
| Alcohol (%) | 13.3 | 13.2 |
| pH | 3.49 | 3.52 |
| Wine color density (a.u.) | 7.0 | 7.1 |
| Wine hue | 0.6 | 0.6 |
| Total phenolics | 26.3 | 25.7 |

Although S-ABA did not affect sugar, total acidity, and anthocyanin/color of grapes at harvest or wine, an experienced sensory panel judged Cabernet Sauvignon wine from the S-ABA treatment as having a longer finish, increased aroma, and greater color intensity than the untreated wine (Table 4).

TABLE 4

Effect of abscisic acid (S-ABA) on Cabernet Sauvignon wine quality (1-5 scale; 1 = low/short; 5 = high/long).

|  | Untreated | S-ABA treated |
|---|---|---|
| Finish | 1.70 | 2.3 |
| Flavor intensity | 3.0 | 2.7 |
| Body/fullness | 2.0 | 1.7 |
| Aroma intensity | 2.3 | 3.7 |
| Color intensity | 3.0 | 4.0 |

Example 3

S-ABA (0.4 grams per vine) was applied to commercially grown Shiraz grapes through the drip irrigation system at approximately 3 weeks prior to initiation of veraison. No surfactant was added to the irrigation water. Results reported are means of 3 replicates. Winemaking followed a standard small lot fermentation protocol with each replicate wine being made from 50 kg of harvested grapes.

Table 5 illustrates that S-ABA increased anthocyanin and phenolics of grape/juice at crush and wine color density and total phenolics and reduced wine hue. S-ABA had no effect on sugar, pH, or total acidity of grapes/juice at crush or on alcohol or pH of wine. Wine made from S-ABA treated Shiraz berries produced a wine that had more intense fruit and was less acidic based on the judging of 6 experienced wine sensory assessors.

TABLE 5

Effect of abscisic acid (S-ABA) on Shiraz grape quality at harvest and wine quality.

|  | Untreated | S-ABA treated |
|---|---|---|
| Grapes/Juice at crush | | |
| Sugar (Be) | 13.7 | 13.6 |
| pH | 3.78 | 3.75 |
| Total acidity | 4.3 | 4.3 |
| Anthocyanins (mg/g) | 0.88 | 1.06 |
| Phenolics (mg/g) | 0.99 | 1.06 |
| Wine | | |
| Alcohol (%) | 13.7 | 13.9 |
| pH | 3.66 | 3.65 |
| Wine color density (a.u.) | 6.66 | 7.87 |
| Wine hue | 0.73 | 0.68 |
| Total phenolics | 34.33 | 37.41 |
| Sensory panel of 6 assessors | — | More intense fruit and less acidic |

Example 4

S-ABA (200 ppm) was applied by foliar spray at veraison to commercially grown Shiraz grapes through standard agricultural spray equipment on 12 Jan. 2007. Kendeen 20 (Tween 20) was added to the spray mix at 50 ml/100 L. Reported results are means of 3 replicates. Winemaking followed a standard small lot fermentation protocol with each replicate wine being made from 50 kg of harvested grapes.

Table 6 shows that S-ABA did not affect sugar, pH, total acidity, anthocyanins, or phenolics of grapes/juice at crush. S-ABA increased color density and total phenolics, but did not affect alcohol, pH, or wine hue. However, wine made from S-ABA treated Shiraz berries produced a wine that had more intense fruit, spice and herbaceous flavors and more tannin based on the judging of 6 experienced wine sensory assessors.

TABLE 6

Effect of abscisic acid (S-ABA) on Shiraz grape quality at harvest and wine quality.

|  | Untreated | S-ABA treated |
|---|---|---|
| Grapes/Juice at crush | | |
| Sugar (Be) | 13.9 | 13.5 |
| pH | 3.84 | 3.85 |
| Total acidity | 3.8 | 3.5 |
| Anthocyanins (mg/g) | 0.93 | 0.92 |
| Phenolics (mg/g) | 1.04 | 1.04 |
| Wine | | |
| Alcohol (%) | 13.7 | 13.8 |
| pH | 3.71 | 3.72 |
| Wine color density (a.u.) | 9.37 | 10.63 |
| Wine hue | 0.55 | 0.53 |
| Total phenolics | 40.1 | 43.4 |
| Sensory panel of 6 assessors | — | More intense fruit, spice and herbaceous. More tannin |

Thus, regardless of the effect of S-ABA on sugar, acidity, anthocyanin/color or phenolics of red grapes at harvest or the subsequent wine made from these berries, these examples illustrate that S-ABA consistently alters the sensory characteristics of the wine such as aroma and flavor.

The invention claimed is:

1. A method of increasing phenolic content of wine comprising:
   (a) applying about 200 ppm S-abscisic acid or its salts by foliar spray to Shiraz grapes or Shiraz grapevines during the time period beginning about 21 days before verasion and ending at the post verasion perion when sugar levels in berries measure approximately 18-20° Brix, and
   (b) using the Shiraz grapes to prepare wine,
   wherein the wine has increased phenolic content and wherein the S-abscisic acid or its salts is applied at a rate of from 25 to 300 gallons per acre.

* * * * *